United States Patent
Iversen et al.

(10) Patent No.: US 9,901,467 B2
(45) Date of Patent: Feb. 27, 2018

(54) ABOVE-KNEE PROSTHESIS

(71) Applicant: Motion Control, Salt Lake City, UT (US)

(72) Inventors: Edwin K. Iversen, Salt Lake City, UT (US); Joseph Anthony Jacobs, Salt Lake City, UT (US); Jeffrey Christenson, Salt Lake City, UT (US)

(73) Assignee: Motion Control, Inc., Salt Lake City, UT (US)

( * ) Notice: Subject to any disclaimer, the term of this patent is extended or adjusted under 35 U.S.C. 154(b) by 121 days.

(21) Appl. No.: 15/099,516

(22) Filed: Apr. 14, 2016

(65) Prior Publication Data
US 2016/0302946 A1    Oct. 20, 2016

Related U.S. Application Data

(60) Provisional application No. 62/147,534, filed on Apr. 14, 2015.

(51) Int. Cl.
| | |
|---|---|
| *A61F 2/64* | (2006.01) |
| *A61F 2/74* | (2006.01) |
| *A61F 2/66* | (2006.01) |
| *A61F 2/70* | (2006.01) |
| A61F 2/60 | (2006.01) |
| A61F 2/68 | (2006.01) |
| A61F 2/80 | (2006.01) |
| A61F 2/50 | (2006.01) |
| A61F 2/76 | (2006.01) |

(52) U.S. Cl.
CPC .............. *A61F 2/642* (2013.01); *A61F 2/644* (2013.01); *A61F 2/6607* (2013.01); *A61F 2/68* (2013.01); *A61F 2/70* (2013.01); *A61F 2/80* (2013.01); *A61F 2002/502* (2013.01); *A61F 2002/5006* (2013.01); *A61F 2002/607* (2013.01); *A61F 2002/608* (2013.01); *A61F 2002/6614* (2013.01); *A61F 2002/6863* (2013.01); *A61F 2002/701* (2013.01); *A61F 2002/704* (2013.01); *A61F 2002/745* (2013.01); *A61F 2002/748* (2013.01); *A61F 2002/7625* (2013.01); *A61F 2002/7635* (2013.01)

(58) Field of Classification Search
CPC .......... A61F 2/642; A61F 2/644; A61F 2/646; A61F 2002/5006; A61F 2002/745
See application file for complete search history.

(56) References Cited

U.S. PATENT DOCUMENTS 5,728,172 A * 3/1998 Krieger ..................... A61F 2/64
602/26

* cited by examiner

*Primary Examiner* — David H Willse
(74) *Attorney, Agent, or Firm* — Thorpe North & Western, LLP.

(57) ABSTRACT

A technology for a prosthetic above-knee device is provided. A socket may be used to attach the device to a residual limb, and may have a rigid body coupled to the socket. The device may include a first link with a first link end coupled through the rigid body to the socket and a second link end coupled to the rigid body. The second link of the device may have a third link end attached to the rigid body, and a fourth link end coupled to a housing. The device may include a hydraulic cylinder with a piston and a hydraulic cylinder link coupled between the rigid body and the piston of the hydraulic cylinder. The stability adjustment nut may adjust a travel distance of the hydraulic cylinder link with respect to the hydraulic cylinder to provide an adjustment of an instant center for stability modification.

20 Claims, 8 Drawing Sheets

ABOVE-KNEE PROSTHESIS

This application claims the priority benefit of U.S. Provisional Patent Application Ser. No. 62/147,534 which is incorporated herein by reference.

BACKGROUND

Prostheses (or prosthetics) are artificial devices that replace body parts (e.g., fingers, hands, arms, legs). Generally, prostheses may be used to replace body parts lost by injury or missing from birth. Existing above knee prostheses use a significant amount of energy to walk and run as compared to the energy that able bodied individuals use. This is due to the fact that existing above knee prostheses have significant energy loss while being used by a patient.

DETAILED DESCRIPTION

Reference will now be made to the examples illustrated in the drawings, and specific language will be used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure are to be considered within the scope of the description.

A technology is provided that involves an above-knee prosthesis for individuals with transfemoral limb loss. This technology is better able to store and release energy and thus individuals or patients who are using the above-knee prosthesis are able to expend less energy when walking or running.

Figure 1:
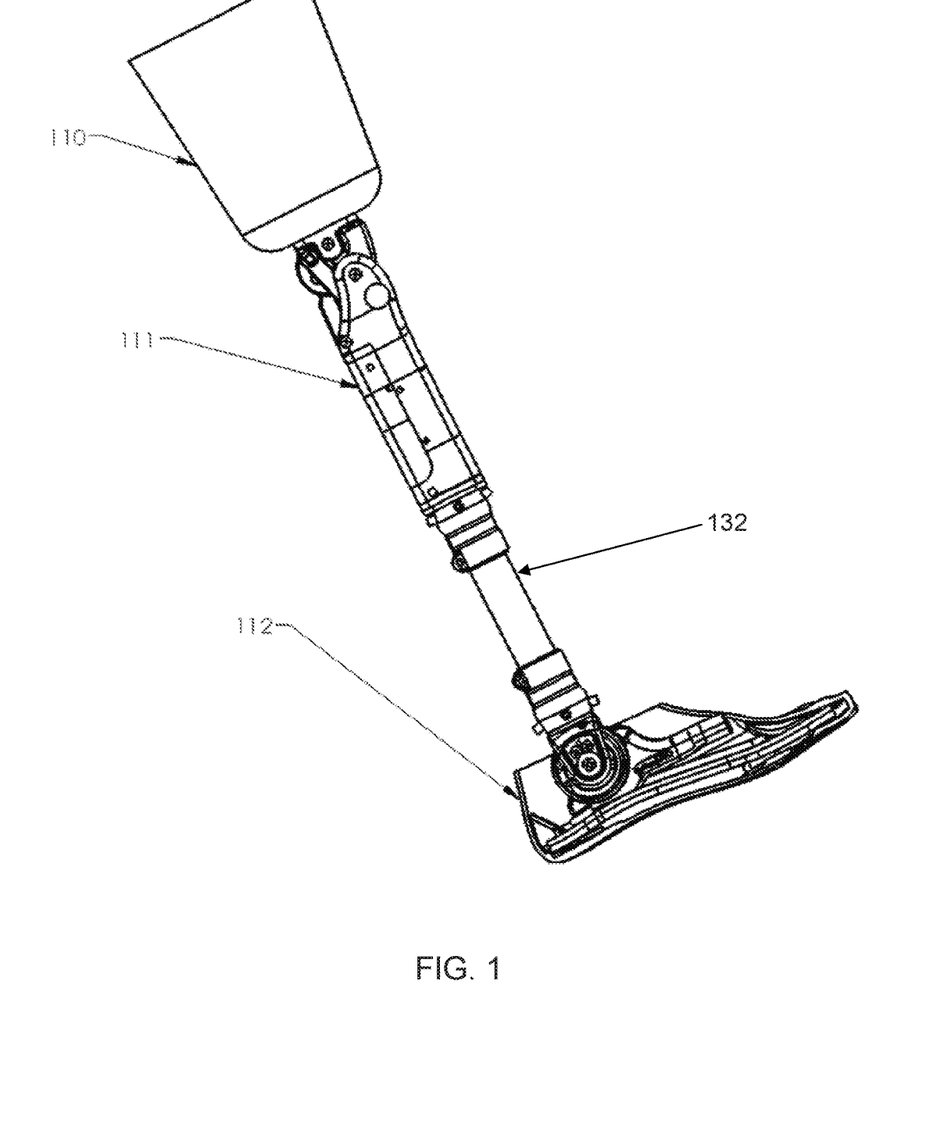
FIG. 1 illustrates an exemplary above-knee prosthesis system.

FIG. 1 illustrates an exemplary above-knee prosthesis system. The above-knee prosthesis system may include a socket 110 for a prosthesis that is formed to receive a patient's residual limb. The above-knee prosthesis 111 may be connected to an energy storing foot/ankle prosthesis 112 which may be microprocessor controlled and may coordinate functions with the above-knee prosthesis. The above-knee prosthesis 111 may be attached to the foot/ankle prosthesis by a pylon 132, and the above knee-prosthesis can be connected to the pylon using an adapter and a pyramid attachment. For example, the above-kneed prosthesis may have a male portion of the pyramid attachment and the pylon may have the female portion of the pyramid attachment or vice versa. In addition, the energy storing foot/ankle prosthesis 112 may be: a microprocessor controlled hydraulic type, an elastomeric type, a spring type, a composite material or another type of active or passive energy storing ankle system.

Existing above knee prostheses use significantly more energy to walk and run than able bodied individuals use. Since the technology of this polycentric above-knee prosthesis is better able to store and release energy, then individuals who are using the above-knee prosthesis are able to expend less energy when walking and running. Reducing the energy used by a patient to walk and run may make the individual able to use the prosthesis for longer periods of time and may make the above-knee prosthesis more comfortable while in use.

Figure 2:
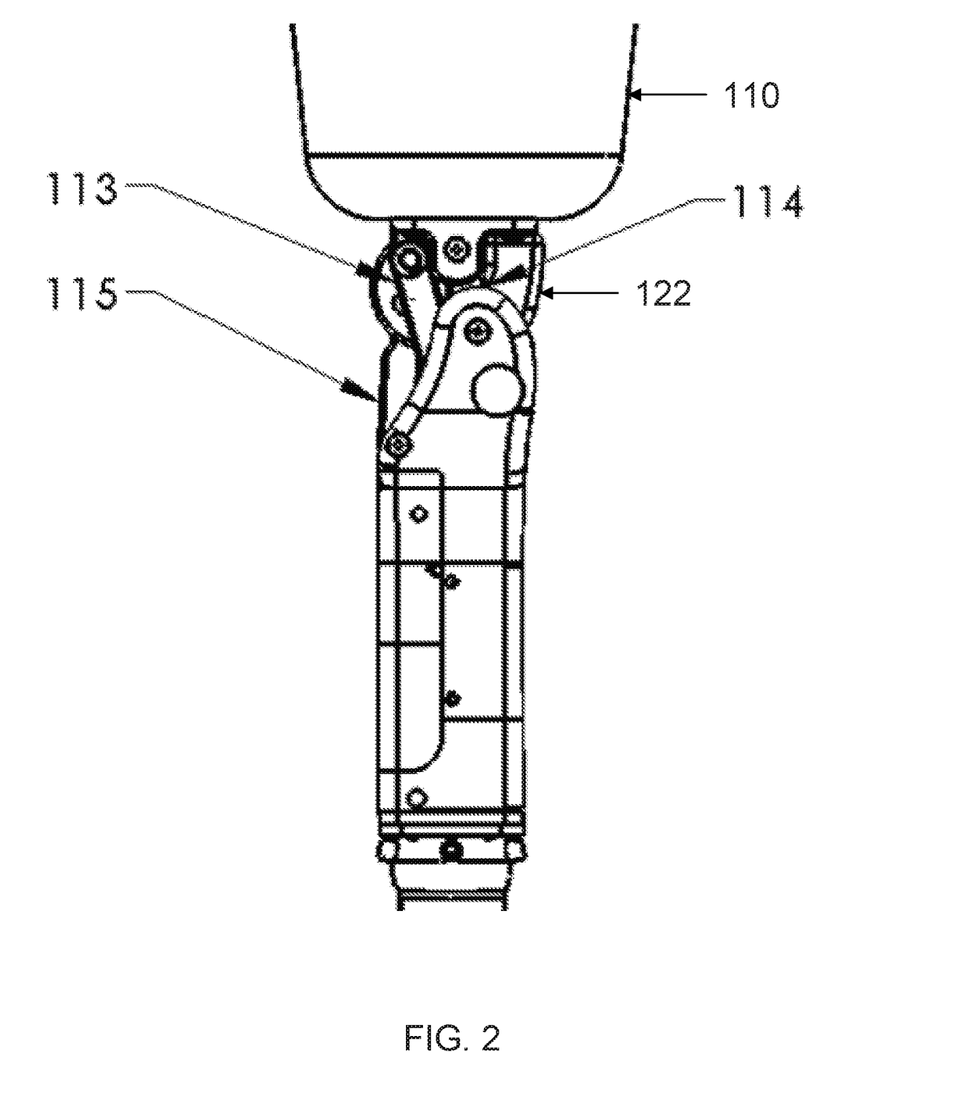
FIGS. 2-5 illustrate polycentric linkages in an exemplary above-knee prosthesis system.

FIG. 2 illustrates an example of a polycentric above-knee prosthesis. More specifically, polycentric linkages may be used that provide low energy control in the onset of the swing phase of the gait cycle. A first link 114 and a second link 115 make up two of the linkages. A hydraulic cylinder link 113 is a third link that is coupled to a hydraulic cylinder that is used to control knee joint impedance. The hydraulic cylinder link 113 can be attached to a rigid body 122 which may act as a fourth link.

Figure 3:
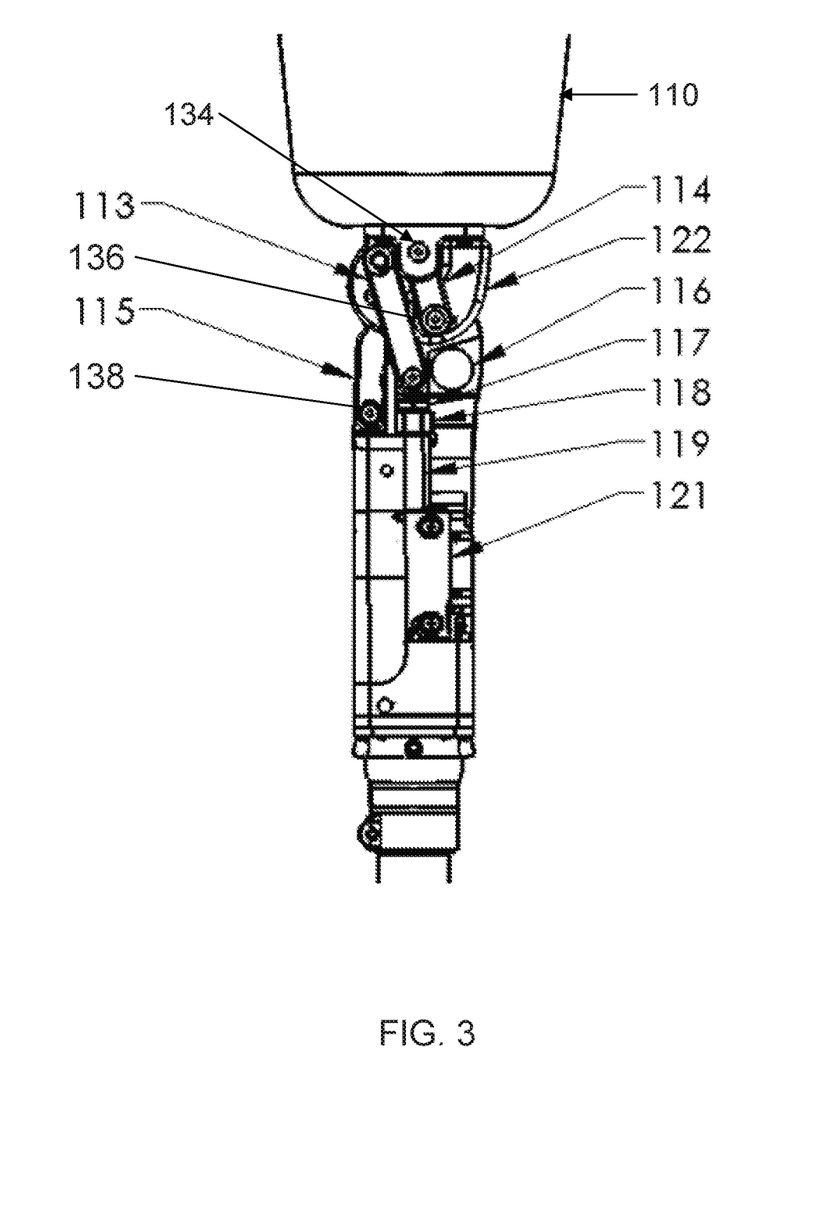

FIG. 3 further illustrates an exemplary above-knee prosthesis system. A first end of the first link 114 may be coupled to a first link axis of rotation 134 (e.g., a pivot or clevis axis) which connects first link 114 to the socket 110 of the prosthesis and connects the rigid body 122 to the socket 110. The coupling may be created using a clevis, a fastener, or another type of rod, pin or fastener. A second end of the first link 114 may be coupled to the rigid body 122 to form a second axis of rotation 136 of the first link. The rigid body 122 may rotate about the first link axis of rotation to assist in providing the moving instant center of the polycentric knee, as will be discussed more later. A first end of a second link 115 may be coupled to the rigid body 122, and a second end 138 of the second link may be coupled to a housing 119 for the polycentric knee. The housing 119 may be an elongated housing that surrounds and protects some components of the polycentric knee. Alternatively, the second link may be connected to the hydraulic cylinder 121 instead of the housing.

In one example configuration, the second link end of the first link may be coupled to the rigid body at a first radial distance from the rotatable coupling (e.g., a knee like joint). In addition, the first link end of the second link may be coupled to the rigid body at a second radial distance from the rotatable coupling. The fourth link end of the second link may be attached the housing.

The hydraulic cylinder link 113 may be coupled to the rigid body 122, at a third radial distance from the rotatable coupling, using a first link end of the hydraulic cylinder link 113 and to the hydraulic cylinder 121 using a second link end of the hydraulic cylinder link 113. Hydraulic valves may also be used that enable fluid to pass from one chamber of the hydraulic cylinder 121 to another chamber of hydraulic cylinder 121. The hydraulic valves may be controlled by a microprocessor or the hydraulic valves may be manually controlled. A battery 116 may also be provided for powering motors which control the hydraulic valves.

The above-knee prosthesis system may include a stability adjustment nut 117, a nut 118 for adjusting the flexion stop, a hydraulic cylinder 121 and hydraulic cylinder link 113. A jam nut can be used for the nut 118 to adjust the stop point of the hydraulic cylinder link 113. The stability adjustment nut 117 may be threaded with the flexion stop nut 118 such that when the stability adjustment nut 117 is turned the distance of the stability adjustment nut from the hydraulic cylinder 121 (e.g., and also optionally the flexion stop nut) increases or decreases, which increases or decreases the travel length or travel path of the hydraulic cylinder link 113 and in turn modifies the stability of the above-knee prosthesis. In one example, the stability adjustment nut 117 maybe threaded inside the flexion stop nut 118. In another example, the stability adjustment nut 117 and the flexion stop nut may be threaded onto a threaded tube or threaded passage which provides a channel for the piston. Alternatively, the stability adjustment nut 117 may be adjacent to the travel channel of the hydraulic cylinder link 113 and piston but still be capable of adjusting the length of the travel of the hydraulic cylinder link 113 by creating a stop point for the hydraulic cylinder link 113.

The stability adjustment may alternatively be a stability adjustment stop using a stop bar, stop surface, stop face, or another stop structure that can engage the hydraulic cylinder link and limit the travel of the hydraulic cylinder link 113. The stability adjustment stop may be adjusted using pre-cut channels, pre-cut notches or other adjustment structures to adjust the travel distance of the hydraulic cylinder link 113.

The hydraulic cylinder 121 may be formed or bored into the material of the housing 119 of the polycentric knee (e.g., the housing 119 may be hydraulic manifold) along with hydraulic passages to enable fluids to enter into and exit from the hydraulic cylinder. Alternatively, the hydraulic cylinder 121 and hydraulic channels may be separate structures that are disposed (or optionally attached) within the housing 119 but are not formed from the material of the housing.

The rigid body 122 may also be covered with a protective cap. In some configurations, the rigid body 122 may be more angular in shape or formed in any shape that allows the linkages to connect as illustrated. However, the protective cap may then cover the rigid body 122 and protect an individual's clothing from damage or protect other individuals from damage that may be caused by coming in contact with the rigid body.

The rigid body 122, first link 114, second link 115 and hydraulic cylinder link 113 may slide in relation to one another in a way that avoids translation movements which may create pinching. For example, the components may slide against one another which may avoid pinching clothing and digits of the patient or another individual. Where there is a gap between components (e.g., the first link 114 and the second link 115), the gap is configured to be large enough to avoid crushing a patent's or another individuals digits (e.g., fingers).

The couplings described may be couplings that use pins, rotatable fasteners, screws, clevis configurations or other known fasteners. The couplings may be rotatable or some couplings may be fixed as needed. For example, a coupling to the housing may be fixed and may not rotate, or the coupling may not be fixed.

Figure 4:
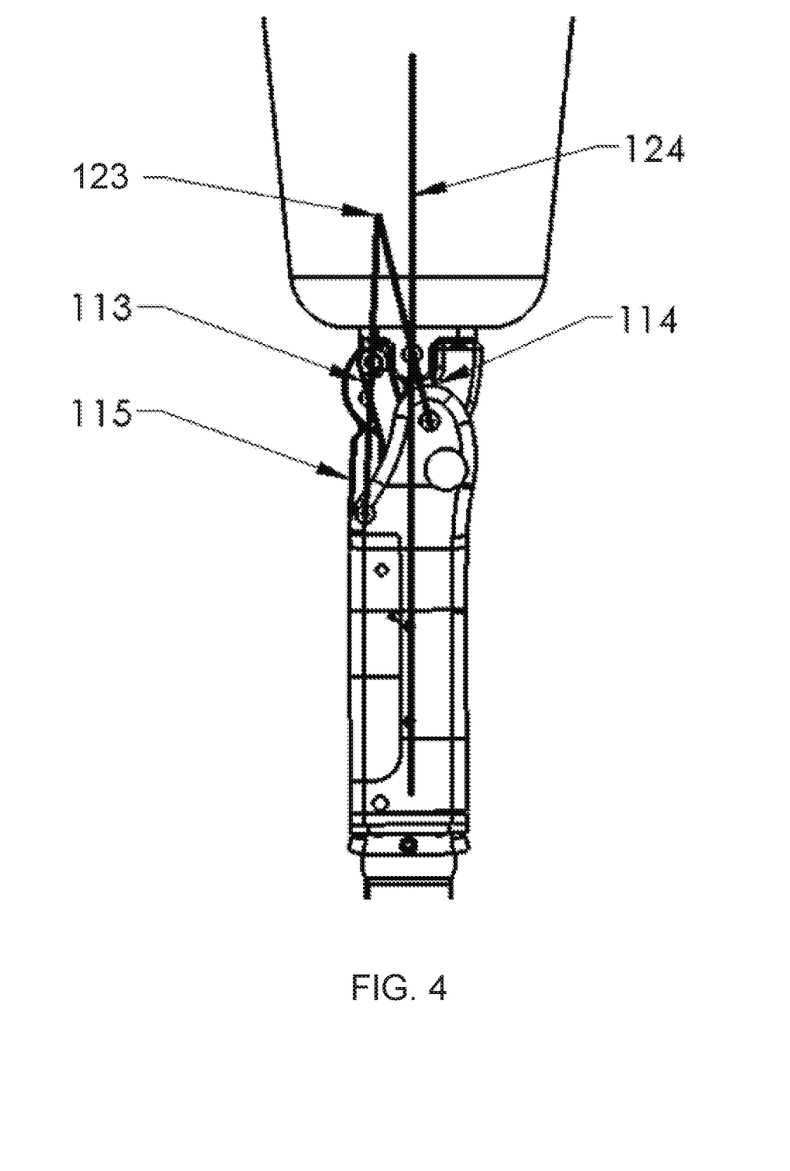

FIG. 4 illustrates an exemplary above-knee prosthesis system. In the configuration shown, the polycentric knee mechanism may be adjusted to be in a more stable condition for individuals that desire a more stable knee. The instant center 123 of the polycentric knee (e.g., a virtual axis of rotation for the prosthetic leg) may be adjusted to be posterior to the load line 124. A line through the centers of the first link 114 and the second link 115 meet at the instant center of the polycentric knee mechanism 123. The connection between the hydraulic cylinder link 113 and the piston of the hydraulic cylinder may have an adjustment to adjust the travel of the hydraulic cylinder link 113. Specifically, the adjustment of the nut 118 affects the travel distance of the hydraulic cylinder link 113 and may provide an adjustment of an instant center for stability modification. By shortening the travel path of the hydraulic cylinder link 113 with respect to the hydraulic cylinder, the instant center 123 may be adjusted. A similar result may be provided by shortening the physical length of the hydraulic cylinder link 113 using a shortening mechanism. The utilization of a polycentric design with energy storing elements may reduce the energy needed to walk and run for a patient with a residual limb.

Figure 5:
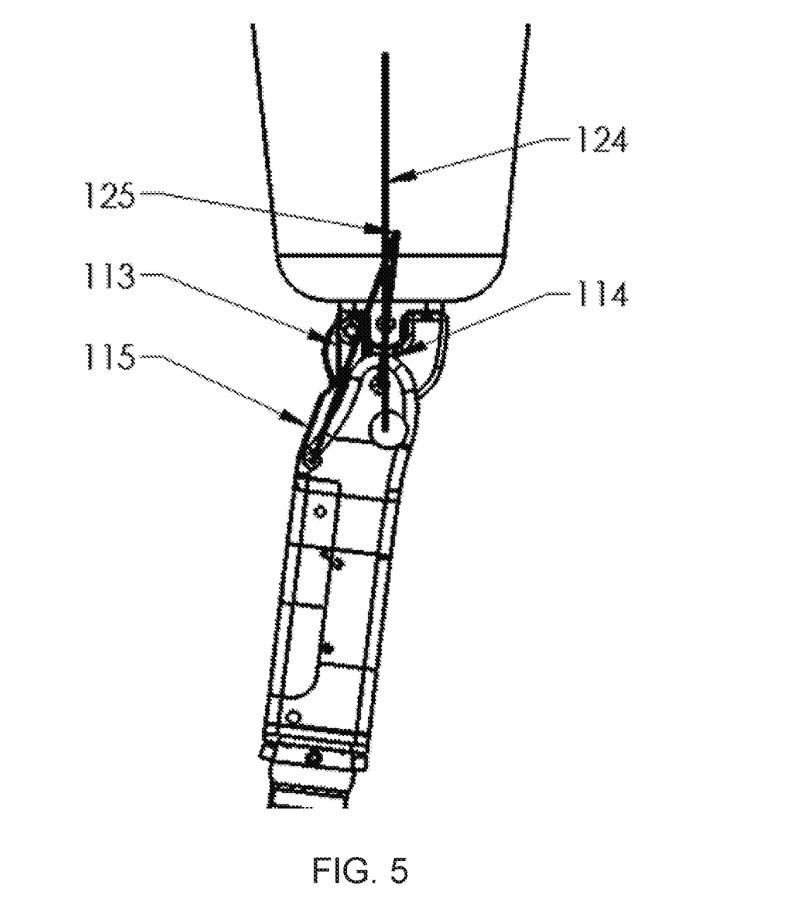

FIG. 5 illustrates an exemplary above-knee prosthesis system. In the configuration shown, the polycentric knee mechanism is adjusted to be in a less stable condition for individuals that desire better voluntary control. The instant center 124 of the polycentric knee 125 is adjusted to be anterior to the load line 124. A line through the centers of the first link 114 and the second link 115 meet at the instant center of the polycentric knee mechanism 123. The movement of the instant center during the gait of the individual may also form a conceptual curve. The instant center 124 (or instant center 123) is a beginning position on this conceptual curve.

Figure 6:
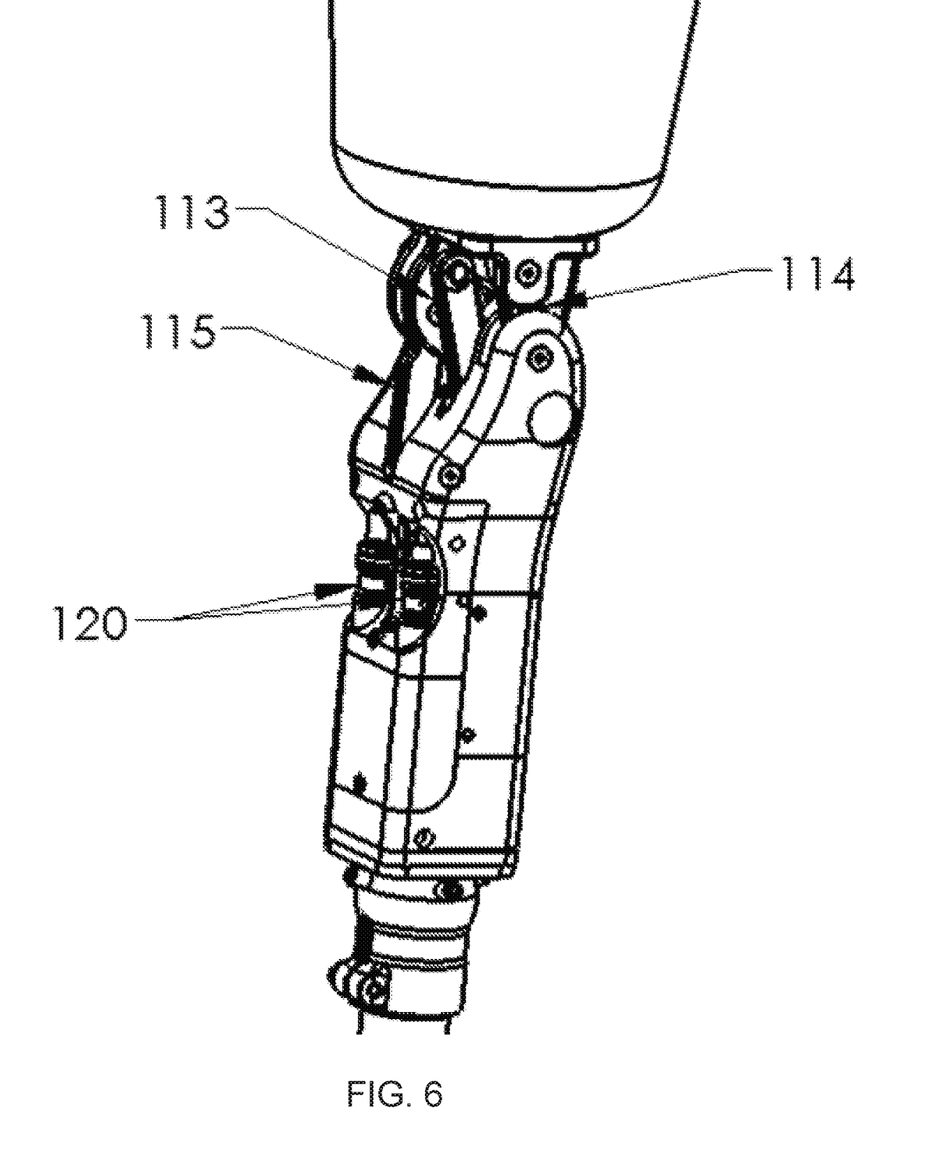
FIG. 6 illustrates a cut away view of an exemplary above-knee prosthesis system showing servo valves that independently control flexion and extension impedance.

FIG. 6 illustrates a cut away view of an exemplary above-knee prosthesis system illustrating servo valves 120 that independently control flexion and extension impedance in a way that minimizes energy consumption. More specifically, the servo valves may limit or allow the flow of fluid between two chambers in the hydraulic cylinder to independently control a viscous resistance to flexion and extension. The cut away on the posterior side of the knee mechanism reveals the two servo valves 120. These servo valves 120 may include an electric motor and rotary hydraulic valve coupled with a check valve that enables the valves to control flexion and extension impedance independently.

Figure 7:
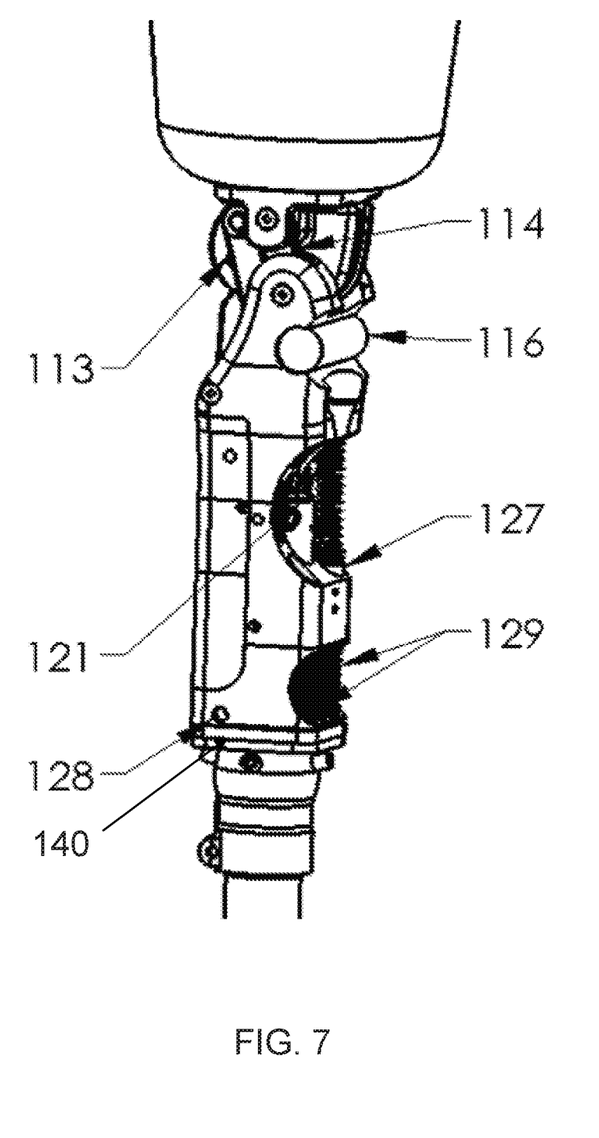
FIG. 7 has a cut away view of an above-knee prosthesis system.

FIG. 7 illustrates an exemplary above-knee prosthesis system. The cutaway on the anterior side of the knee mechanism reveals the hydraulic cylinder 121. A hydraulic accumulator 127 is provided in fluid connection to the hydraulic cylinder 121 to avoid cavitation and to supply oil to the system when slight leaks and evaporation of oil may occur from the hydraulic actuation link (e.g., to supply oil if some oil loss occurs). Two gas springs 129 may provide a stance flex feature to store and release energy during the stance phase of gait. A battery (e.g., lithium ion battery) 116 may be used that to provide power for the servo valves.

The prosthetic above-knee device may include a load sensor 128 consisting of a hinged member or hinged plate that is spring loaded (e.g., using a spring loaded clevis) with respect to a base plate 140, such that toe or heel load flexes and extends a hinged joint in order to change the distance between a magnet and a Hall effect device. A microprocessor may be configured to receive an output of the Hall effect device (e.g., a moment of force on the heel or toe produces) and may determine a level of knee joint impedance to facilitate energy efficient gait.

Figure 8:
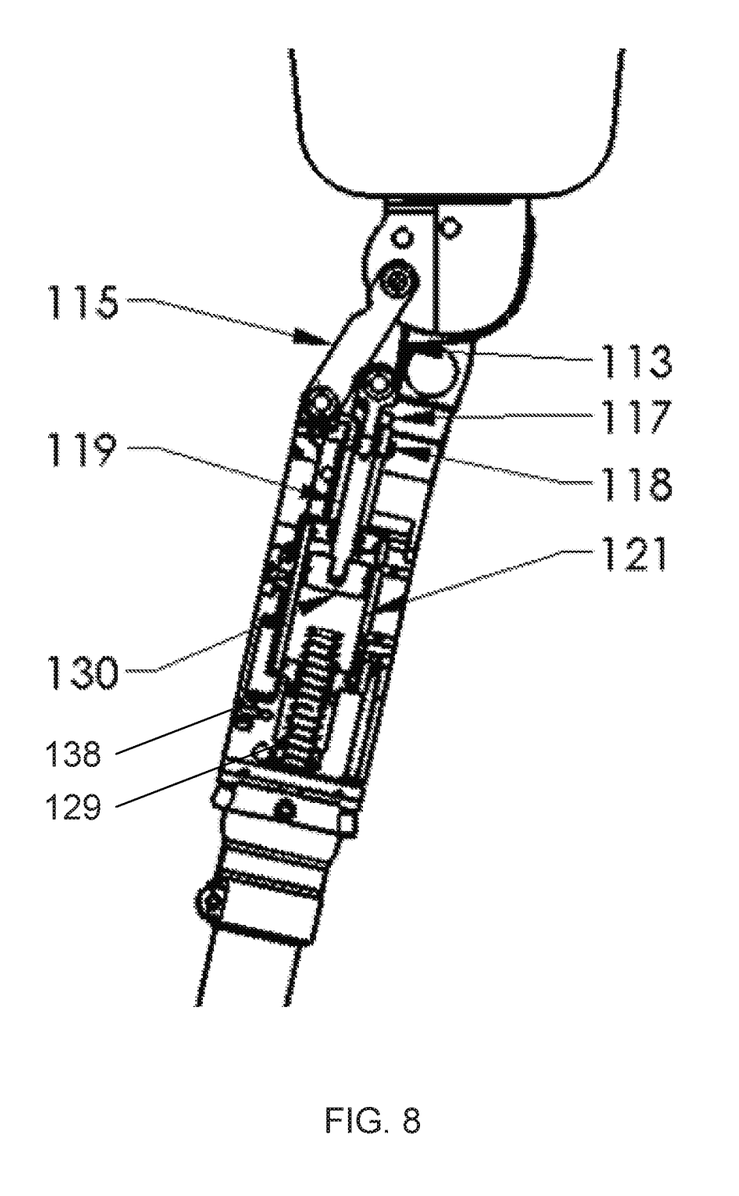
FIG. 8 is a cross sectional view of the above knee prosthesis system.

FIG. 8 illustrates a cross section of the above-knee prosthesis system to illustrate a cross sectional view of the hydraulic cylinder 121 and a piston 130 in the hydraulic cylinder. Hydraulic valves 120 may also be used in combination with the hydraulic cylinder 121, and the hydraulic valves 120 may be controlled by the microprocessor or manually controlled. A battery 116 may also be provided for powering motors which control the hydraulic valves 120. FIG. 8 further illustrates the gas spring 129 system in the hydraulic cylinder which is engaged by the motion of the piston. Thus, viscous impedance is provided by diverting fluid from one side of the cylinder to the other and a second impedance is provided which is a spring impedance by displacing the gas spring using the piston.

Reference was made to the examples illustrated in the drawings, and specific language was used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

What is claimed is:

1. A prosthetic above-knee device, comprising:
   a socket formed to receive a residual limb;
   a housing configured to house portions of the above-knee device;
   a rigid body rotatably coupled to the socket;
   a first link having a first link end having a rotatable coupling to the socket through the rigid body and a second link end coupled to the rigid body;
   a second link having a third link end coupled to the rigid body and a fourth link end coupled to the housing;
   a hydraulic cylinder having a piston;
   a hydraulic cylinder link coupled to the rigid body and the piston of the hydraulic cylinder; and
   a stability adjustment nut to adjust a travel distance of the hydraulic cylinder link with respect to the hydraulic cylinder in order to provide an adjustment of an instant center for stability modification.

2. A prosthetic above-knee device as in claim 1, wherein:
   the second link end of the first link is coupled to the rigid body at a first radial distance from the rotatable coupling; and
   the third link end of the second link is coupled to the rigid body at a second radial distance from the rotatable coupling.

3. A prosthetic above-knee device as in claim 1, wherein the hydraulic cylinder is attached to the housing.

4. A prosthetic above-knee device as in claim 1, further comprising:
   a nut on the hydraulic cylinder link configured to provide a flexion adjustment.

5. A prosthetic above-knee device of claim 1, further comprising:
   a plurality of servo valves that independently control a viscous resistance to flexion and extension.

6. A prosthetic above-knee device of claim 5, further comprising:
   gas springs in the hydraulic cylinder that are engaged or disengaged by fluid passing through the servo valves in order to control fluid impedance of flexion and extension of the prosthetic above-knee device by storing and releasing energy during a stance phase of a gait cycle.

7. A prosthetic above-knee device of claim 5, wherein the servo valves are electronically controlled.

8. A prosthetic above-knee device of claim 5, wherein the servo valves comprise an electric motor, and a rotary hydraulic valve coupled with a check valve.

9. A prosthetic above-knee device as in claim 1, with a polycentric knee joint and a load sensor consisting of a hinged plate that is spring loaded such that toe or heel loads flex and extend a hinged joint changing a distance between a magnet and a Hall effect device.

10. A prosthetic above-knee device as in claim 9, further comprising a microprocessor configured to receive an output of the Hall effect device and determine a level of knee joint impedance to facilitate energy efficient gait.

11. A prosthetic above-knee device as in claim 1, further comprising a hydraulic accumulator in fluid connection to the hydraulic cylinder to avoid cavitation and to supply oil if oil loss occurs.

12. A prosthetic above-knee device as in claim 5, further comprising, a battery to provide power for the plurality of servo valves.

13. A prosthetic above-knee device, comprising:
    a socket formed to receive a residual limb;
    a rigid body coupled to the socket;
    a first link having the first end coupled to a socket and a second end coupled to the rigid body;
    a hydraulic cylinder;
    a hydraulic cylinder link coupled to the hydraulic cylinder; and
    a stability adjustment stop to adjust a travel distance of the hydraulic cylinder link with respect to the hydraulic cylinder in order to provide an adjustment for stability modification.

14. A prosthetic above-knee device as in claim 13, further comprising:
    a nut on the hydraulic cylinder link configured to provide a flexion adjustment.

15. A prosthetic above-knee device of claim 13, further comprising:
    a plurality of servo valves that control a viscous resistance to flexion and extension.

16. A prosthetic above-knee device of claim 15, further comprising:
    gas springs in the hydraulic cylinder that engage or disengage by fluid passing through the servo valves in order to control an impedance of flexion and extension of the knee by storing and releasing energy during a stance phase of a gait cycle.

17. A prosthetic above-knee device of claim 15, wherein the plurality of servo valves comprise an electric motor, a rotary hydraulic valve coupled with a check valve, and a battery to provide power for the plurality of servo valves.

18. A prosthetic above-knee device as in claim 13, with a polycentric knee joint and a load sensor consisting of a hinged joint that is spring loaded such that toe or heel loads flex and extend the hinged joint changing the distance between a magnet and a Hall effect device.

19. A prosthetic above-knee device as in claim 18, further comprising a microprocessor configured to receive an output of the Hall effect device and determine a level of knee joint impedance to facilitate energy efficient gait.

20. A prosthetic above-knee device, comprising:
    a socket formed to receive a residual limb;

a housing configured to house portions of the above-knee device;

a rigid body rotatably coupled to the socket;

a first link having a first link end rotatably coupled to the socket and a second link end coupled to the rigid body;

a second link coupled between the rigid body and the housing;

a hydraulic cylinder;

a stability adjustment stop to adjust a travel distance of a hydraulic cylinder link with respect to the hydraulic cylinder in order to provide an adjustment for stability modification;

a plurality of servo valves to control fluid flow from and to the hydraulic cylinder and to modify a viscous resistance for flexion and extension;

a Hall effect device to measure a moment of force on a heel or toe; and a microprocessor configured to receive an output of the Hall effect device and determine a level of knee joint impedance using the plurality of servo valves to facilitate energy efficient gait by controlling the plurality of servo valves.

\* \* \* \* \*